US012734295B2

(12) United States Patent
Juretich et al.

(10) Patent No.: US 12,734,295 B2
(45) Date of Patent: Sep. 15, 2026

(54) METHOD TO DELIVER REMAINING LIQUID IN AN ENTERAL OR OTHER INFUSION DEVICE

(71) Applicant: ZEVEX, INC., Salt Lake City, UT (US)

(72) Inventors: Jeffery T. Juretich, Herriman, UT (US); Jeffrey D. Geisler, Salt Lake City, UT (US); John Bacon, Provo, UT (US); David Thorne, Kaysville, UT (US)

(73) Assignee: Zevex, Inc., Salt Lake City, UT (US)

( * ) Notice: Subject to any disclaimer, the term of this patent is extended or adjusted under 35 U.S.C. 154(b) by 1143 days.

(21) Appl. No.: 17/432,968

(22) PCT Filed: Mar. 18, 2020

(86) PCT No.: PCT/US2020/023240
§ 371 (c)(1),
(2) Date: Aug. 23, 2021

(87) PCT Pub. No.: WO2020/197867
PCT Pub. Date: Oct. 1, 2020

(65) Prior Publication Data

US 2022/0152299 A1 May 19, 2022

Related U.S. Application Data

(60) Provisional application No. 62/822,458, filed on Mar. 22, 2019.

(51) Int. Cl.
*A61M 5/168* (2006.01)
*A61M 5/14* (2006.01)
(Continued)

(52) U.S. Cl.
CPC ...... *A61M 5/1684* (2013.01); *A61M 5/14228* (2013.01); *A61M 5/172* (2013.01);
(Continued)

(58) Field of Classification Search
CPC ............ A61M 5/1684; A61M 5/16831; A61M 5/16845; A61M 5/1685; A61M 5/16854;
(Continued)

(56) References Cited

U.S. PATENT DOCUMENTS 6,339,718 B1 1/2002 Zatezalo et al.
2002/0007116 A1 1/2002 Zatezalo et al.
(Continued)

OTHER PUBLICATIONS

Zevex, Incorporated, Zevex Enteral Nutrition Delivery Systems, Infinity Orange Small Volume Enteral Feeding Pump Operator's Manual, 2008, U.S.A.

*Primary Examiner* — Kevin C Sirmons
*Assistant Examiner* — Leah J Swanson
(74) *Attorney, Agent, or Firm* — Hodgson Russ LLP

(57) ABSTRACT

A waste-reducing pumping system and method for delivering a liquid to a patient according to a predetermined therapy protocol is characterized by a stored flush mode routine executable by a processor after an end-of-therapy stoppage of a pumping mechanism, whereby the pumping mechanism is operated to deliver residual liquid remaining in downstream tubing of an administration set to the patient to prevent the residual liquid from being wasted or manually administered at an unsafe rate.

11 Claims, 4 Drawing Sheets

(51) Int. Cl.
*A61M 5/142* (2006.01)
*A61M 5/172* (2006.01)
*F04B 43/08* (2006.01)

(52) U.S. Cl.
CPC ..... *F04B 43/08* (2013.01); *A61M 2005/1403* (2013.01); *A61M 2205/3327* (2013.01); *A61M 2205/3379* (2013.01); *A61M 2205/3389* (2013.01); *A61M 2205/502* (2013.01)

(58) Field of Classification Search
CPC .............. A61M 5/16859; A61M 5/168; A61M 5/16804; A61M 5/172; A61M 5/36; A61M 5/365; A61M 5/14228; A61M 5/14232; A61M 2005/1403; A61M 2005/14208; A61J 15/0078; A61J 15/008; F04B 43/08; F04B 43/082; F04B 43/09; F04B 43/12; F04B 43/1253; F04B 49/02; F04B 49/06; F04B 49/065
See application file for complete search history.

(56) References Cited

U.S. PATENT DOCUMENTS

2002/0127114 A1 9/2002 Barak
2007/0118078 A1 5/2007 McNally et al.
2008/0119822 A1* 5/2008 Knauper ............. A61J 15/0076 604/151
2009/0012442 A9 1/2009 Brugger et al.
2009/0048583 A1 2/2009 Williams et al.
2010/0137778 A1 6/2010 Kunjan et al.
2010/0137802 A1 6/2010 Yodfat et al.
2013/0345658 A1 12/2013 Browne et al.
2014/0358077 A1 12/2014 Oruklu et al.
2015/0025453 A1* 1/2015 Ledford ................ A61M 5/168 604/67
2015/0231363 A1 8/2015 Uber et al.
2016/0030292 A1* 2/2016 Hyun ...................... A23L 33/40 604/113
2018/0263855 A1 9/2018 Hyun et al.
2019/0060566 A1 2/2019 Ledford et al.

* cited by examiner

METHOD TO DELIVER REMAINING LIQUID IN AN ENTERAL OR OTHER INFUSION DEVICE

CROSS-REFERENCE TO RELATED APPLICATION

The present application claims priority and benefit of U.S. Provisional patent Application No. 62/822,458 filed Mar. 22, 2019, the entire contents of which are incorporated herein by reference.

FIELD OF THE DISCLOSURE

The present disclosure relates to the field of medical infusion pumps, for example enteral feeding pumps and intravenous medication pumps, for delivering liquid to a patient in a controlled manner.

BACKGROUND OF THE DISCLOSURE

Programmable infusion pumps for delivering nutritional liquids and medicine to a patient in accordance with predetermined liquid delivery parameters are in wide usage. One type of medical pump is a peristaltic pump arranged along flexible connective tubing of an administration set carrying liquid from a liquid source to the patient. The peristaltic pump has a pumping mechanism for progressively squeezing successive portions of the tubing to cause fluid to flow through the tubing in a flow direction toward the patient. In a common arrangement, the pumping mechanism may include a motor-driven wheel having radial fingers or rollers that engage a segment of the tubing arranged about a circumferential portion of the wheel. As the wheel rotates, fluid is pumped through the tubing to the patient. The tubing segment arranged about the pump wheel may be held in a U-shaped configuration by a cassette of the administration set designed for receipt in a channel or receptacle area of the pump. The cassette may provide terminals for connecting an incoming line of tubing coming from the liquid source and an outgoing line of tubing going to the patient to opposite ends of the U-shaped tubing segment received by the pump. Other pump configurations using linear and curvilinear pumping mechanisms rather than a rotary pumping mechanism are also known. Tubing extending from the liquid source to the pumping mechanism is sometimes referred to as "upstream" tubing, and tubing extending from the pumping mechanism to the patient is sometimes referred to as "downstream" tubing.

As a safety feature, it is known to provide an air-in-line ("AIL") sensor on the infusion pump for detecting an air-in-line condition and triggering an alarm to prevent delivery of air to the patient. For example, the AIL sensor may include an ultrasonic transmitter arranged to direct ultrasound through the tubing and a receiver on an opposite side of the tubing from the transmitter for receiving the ultrasound waves after passage through the tubing and the fluid carried thereby. The receiver generates an output signal indicating whether the ultrasound signal passed through liquid or air as it travelled from the transmitter to the receiver. The AIL sensor output is sampled regularly as fluid is pumped through the tubing to observe each incremental volume of fluid passing through the sensor's zone of observation, and an AIL condition is recognized when a continuous volume of air reaches a predetermined threshold. The AIL sensor signal may also be evaluated to determine an end of therapy condition when there is no more liquid remaining at the liquid source. Alternatively, or additionally, an end of therapy condition may be determined based on a signal from a liquid level sensor or liquid volume sensor associated with the liquid source.

A recognized disadvantage of known medical pumps is that the pump motor is commanded to stop by a pump controller (e.g. a programmed microprocessor in the pump) in response to an end of therapy determination made by the controller based on a signal from an AIL sensor and/or a liquid volume or liquid level sensor as described above, thereby leaving a quantity of liquid stranded in the downstream portion of the tubing. In some cases, the stranded residual liquid may be delivered to the patient by manually priming out the remaining liquid either by using a priming feature of the pump or by gravity priming. However, using the priming feature of the pump or gravity priming may deliver liquid at a rate intolerable to the patient, and these methods require the full attention of the caregiver to deliver the liquid to the end of the downstream tubing and then stop delivery. In many cases, rather than trying to deliver the residual liquid, the caregiver simply wastes the residual liquid by disposing of the used administration set with the residual liquid still in the downstream tubing. The wasted liquid is often expensive nutritional or medicinal liquid, or precious mother's milk.

There is a need to make delivery of residual liquid in downstream tubing easier for the caregiver, and safer and more tolerable for the patient.

SUMMARY OF THE DISCLOSURE

The present disclosure provides a waste-reducing pumping system and method for delivering a liquid to a patient according to a predetermined therapy protocol, for example a protocol for continuous infusion of the liquid at a predetermined delivery rate. More particularly, the system and method enable execution of a flush mode routine to deliver residual liquid remaining in administration set tubing after an end-of-therapy condition is reached, residual liquid that heretofore may have been wasted or manually administered to the patient at an unsafe rate.

The pumping system may generally comprise a source of the liquid, an administration set, a pumping mechanism, a processor, at least one sensor associated with the administration set and/or the source, and at least one memory module including stored program instructions executable by the processor.

The administration set may be arranged to carry the liquid from the source to the patient, and may include a tubing segment, upstream tubing communicating from the source to the tubing segment, and downstream tubing communicating from the tubing segment to the patient. The pumping mechanism may be arranged to engage the tubing segment of the administration set. The pumping mechanism may include a motor operable to actuate at least one pumping member to peristaltically deform the tubing segment to force the liquid through the tubing segment in a direction from the upstream tubing toward the downstream tubing, and a motor controller providing control commands to the motor. The at least one sensor may generate an end-of-therapy signal indicating an end-of-therapy condition, wherein the end-of-therapy signal is transmitted to the processor.

The processor may be connected to the motor controller, and may execute program instructions stored by the at least one memory module for operating the motor to control operation of the pumping mechanism.

In accordance with the present disclosure, the stored program instructions may include a flush mode routine executable by the processor to operate the pumping mechanism in a flush mode to deliver residual liquid present within the downstream tubing to the patient after the processor receives the end-of-therapy signal.

The delivery method may generally comprise automatically operating a pumping mechanism in accordance with the predetermined therapy protocol to deliver the liquid from a source to the patient by way of an administration set, detecting an end-of-therapy condition and automatically stopping operation of the pumping mechanism when the end-of-therapy condition is detected, prompting a user regarding execution of a flush mode routine for operating the pumping mechanism to deliver residual liquid in the administration set to the patient, and initiating execution of the flush mode routine in response to a user input action.

BRIEF DESCRIPTION OF THE DRAWING VIEWS

DETAILED DESCRIPTION OF THE INVENTION

Figure 1:
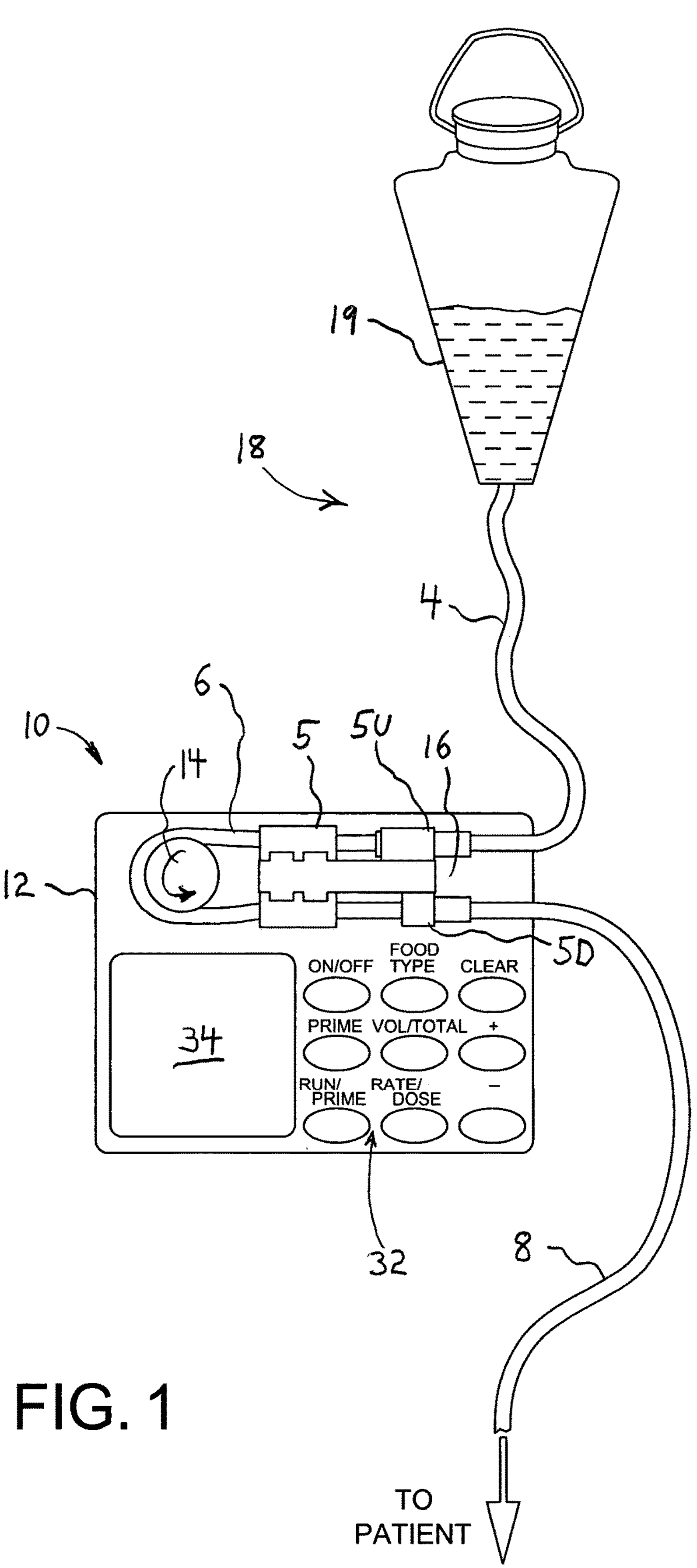
FIG. 1 is a schematic representation of a medical infusion pumping system formed in accordance with an embodiment of the present disclosure.
Figure 2:
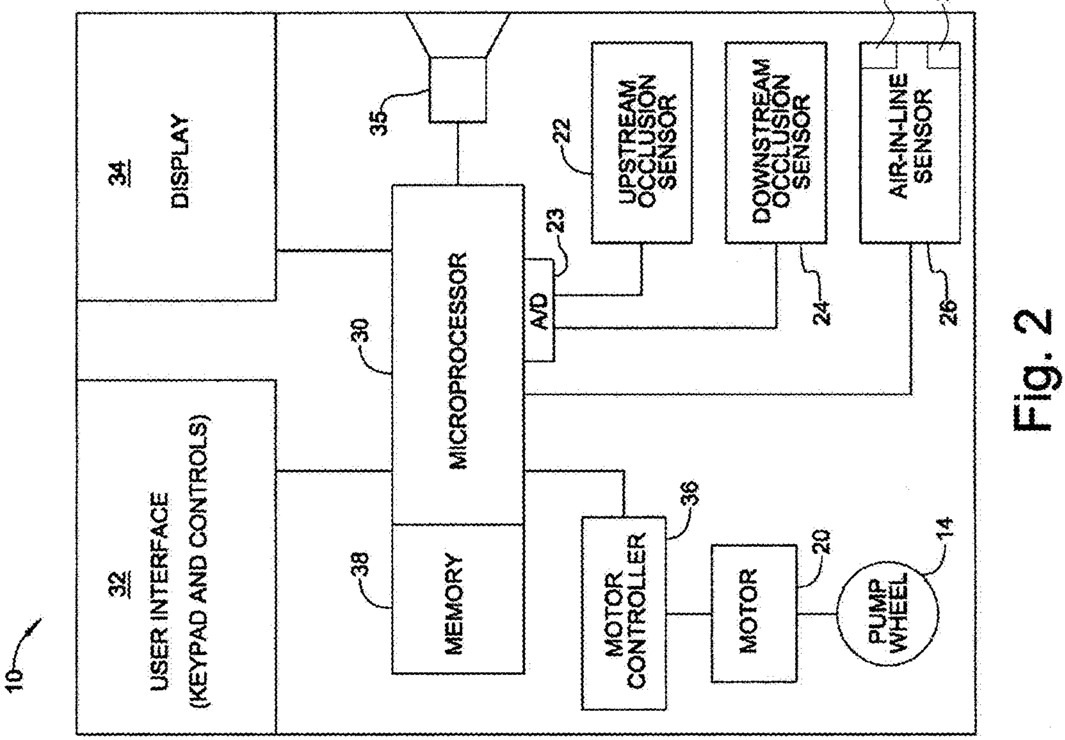
FIG. 2 is an electronic block diagram of an infusion pump of the pumping system shown in FIG. 1.

FIGS. 1 and 2 schematically depict a programmable infusion pump 10 embodying the present disclosure. Infusion pump 10 includes a housing 12, a pump wheel or rotor 14 and a cassette receptacle 16 on an external face of the housing, and a door (not shown) connected to the housing to open and close over the cassette receptacle and pump wheel. As shown in FIG. 1, an administration set 18 may be installed in association with the pump for carrying fluid from a fluid source 19 to a patient. The administration set may include upstream tubing 4 running from the fluid source 19 to the pump 10, downstream tubing 8 running from the pump to a patient, a cassette 5 received in cassette receptacle 16, and a U-shaped tubing segment 6 arranged around pump wheel 14. Cassette 5 is configured with connection terminals 5U and 5D for connecting upstream tubing 4 to an upstream end of tubing segment 6 and downstream tubing 8 to a downstream end of tubing segment 6 to complete a flow path from the upstream tubing to the downstream tubing via the pump.

Pump wheel 14 is part of a pumping mechanism operable to cause fluid flow through the tubing in an intended flow direction. The pumping mechanism further includes an electric motor 20 connected to pump wheel 14 and operable to rotate the pump wheel about its axis. Pump wheel 14 has radial fingers or rollers (not shown) that engage tubing segment 6 arranged about a circumferential portion of the wheel. When pump wheel 14 rotates, successive portions of tubing segment 6 are progressively squeezed to cause fluid to flow through the tubing in a flow direction toward the patient. The flow rate of infused fluid may be controlled by controlling the rate at which motor 20 is driven and/or the length of time motor 20 is driven at a given rate. Those skilled in the art will understand that variations of the peristaltic pumping mechanism described above are possible. For example, motor 20 may drive a cam member connected to a series of parallel fingers or rollers arranged side-by-side, whereby peristaltic pumping action is applied to a straight segment of tubing instead of a curved segment of tubing as shown in FIG. 1. The present disclosure is not limited to a specific pumping mechanism configuration.

Infusion pump 10 may include an upstream occlusion sensor 22 at a location along tubing segment 6 upstream from pumping wheel 14 and a downstream occlusion sensor 24 at a location along tubing segment 6 downstream from pumping wheel 14. Upstream sensor 22 and downstream sensor 24 each provide a respective sensor signal indicative of a respective local fluid pressure in the tubing. For example, upstream and downstream sensors 22, 24 may be transducers or strain gauges arranged to engage an outer wall of tubing segment 6 to detect deflection of the flexible tubing wall caused by fluid pressure within the tubing and provide an electronic signal proportional to the deflection.

Infusion pump 10 further includes an air-in-line (AIL) sensor 26 for detecting whether a volume of fluid observed by the sensor at a given time is air or liquid. In the present embodiment, AIL sensor 26 may comprise an ultrasonic transducer which includes a pair of piezoelectric ceramic elements 26A and 26B opposing each other across a portion of tubing segment 6. One ceramic element 26A is driven by microprocessor 30 at a frequency that sweeps through the resonance which lies within the frequency range. The ultrasonic energy is transmitted by element 26A into one side of the tubing and a portion of the energy is received by element 26B on the other side. If liquid is present in the tubing, the ultrasonic energy received by element 26B will be greater than a preset comparator threshold and is then converted into a logic level of "High". If air is present in the tubing, the medium for propagating the ultrasonic energy is less dense and the signal generated by element 26B is attenuated below the threshold and is converted into a logic level of "Low". Thus, in the embodiment just described, the amplitude of the ultrasonic energy which is received by element 26B is the main principle for determining the difference between liquid and air within the tubing. The tubing may be dry-coupled to the AIL sensor elements 26A and 26B; i.e. the sensor arrangement does not require the use of ultrasonic gel. As an alternative to ultrasonic AIL detection, an AIL sensor based on detection of optical properties of air and liquid media may be used.

Infusion pump 10 is configured to permit a user to select and/or create, and then run, an infusion therapy protocol which may specify the rate at which the liquid is to be delivered to the patient. The protocol may be a "continuous therapy" protocol having no predefined total dosage amount, or the protocol may further specify the total amount of liquid to be delivered to the patient. Infusion pump 10 includes a microprocessor 30 connected to a user interface 32 having input devices such as a keypad, switches and dial controls. Infusion pump 10 also includes a display 34 connected to microprocessor 30. Display 34 may be a touch screen display acting at times as part of user interface 32. Microprocessor 30 is connected to a motor controller 36 for driving electric motor 20 to administer a chosen therapy protocol. One or more memory modules 38 are connected to or integrated with microprocessor 30 for storing instructions executable by the microprocessor for controlling pump operation. The stored instructions may be organized in software routines. Among the stored software routines are routines that detect an end of therapy condition and enable the user to operate pump 10 in a flush mode to deliver residual liquid present within downstream tubing 8 to the patient. These routines are described in detail below. For purposes of the present disclosure, microprocessor 30 may receive a signal from AIL sensor 26. Alternatively, or additionally, microprocessor 30 may receive a signal from a liquid level or liquid volume sensor (not shown) associated with liquid source 19. Microprocessor 30 is also connected to upstream occlusion sensor 22 and downstream occlusion sensor 24. Analog-to-digital conversion circuitry 23 is shown for converting the analog voltage signals from the occlusion sensors to digital form for use by microprocessor 30, however other forms of occlusion sensor and microprocessor interfaces may be used. Infusion pump 10 may also include an audible signal generator 35 connected to microprocessor 30.

Figure 3:
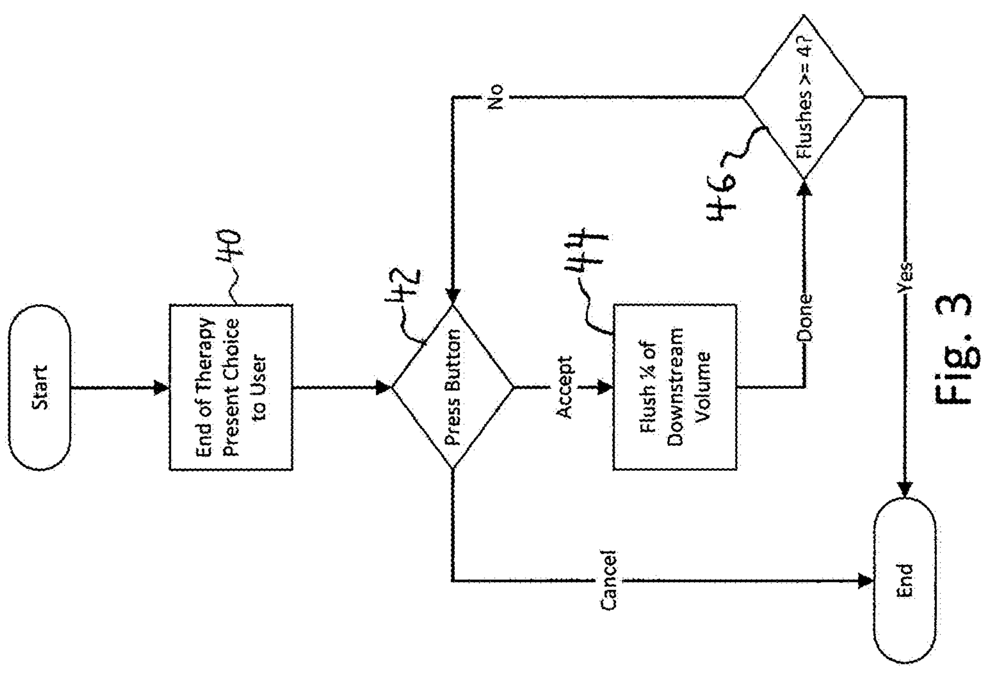
FIG. 3 is a flow diagram illustrating methodology for delivering residual liquid from downstream tubing of an administration set when the pump is in a flush mode in accordance with an embodiment of the present disclosure.
Figure 4:
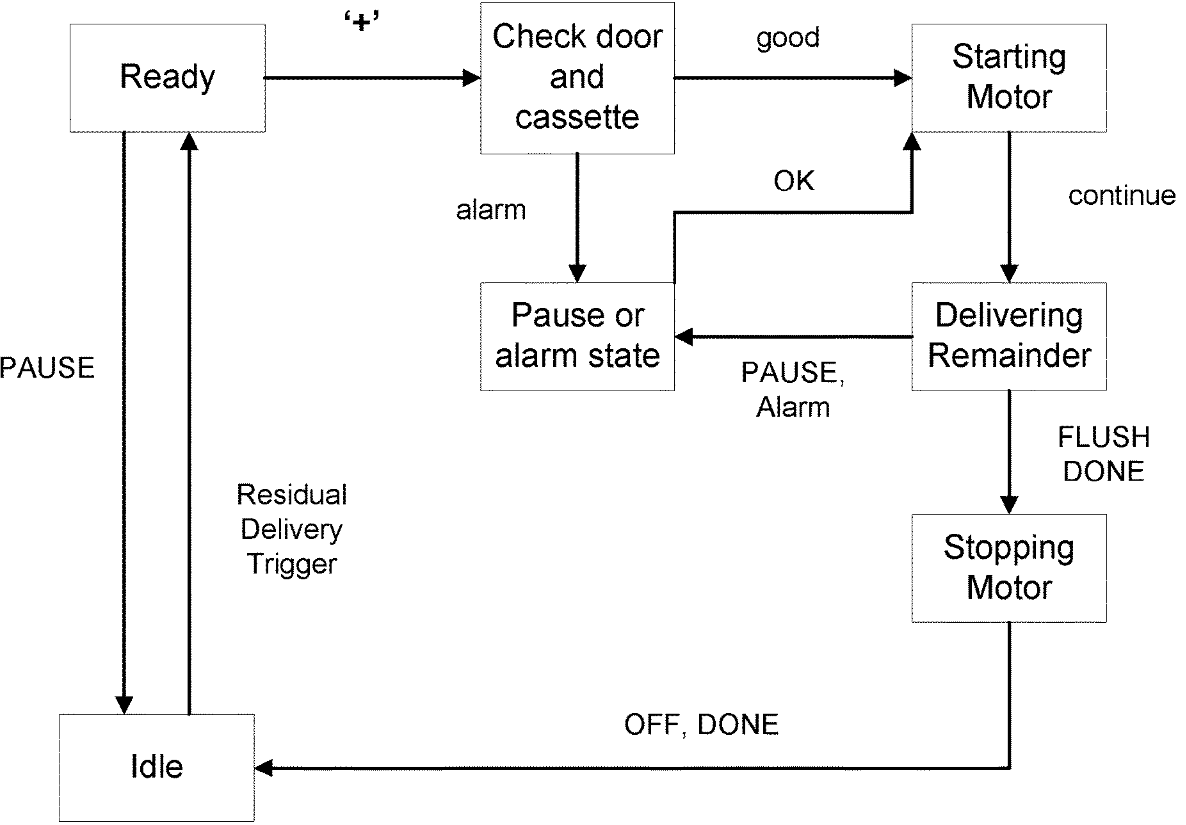
FIG. 4 is a state machine diagram illustrating programmed behavior of the pump associated with the flush mode in accordance with an embodiment of the present disclosure.
Figure 5:
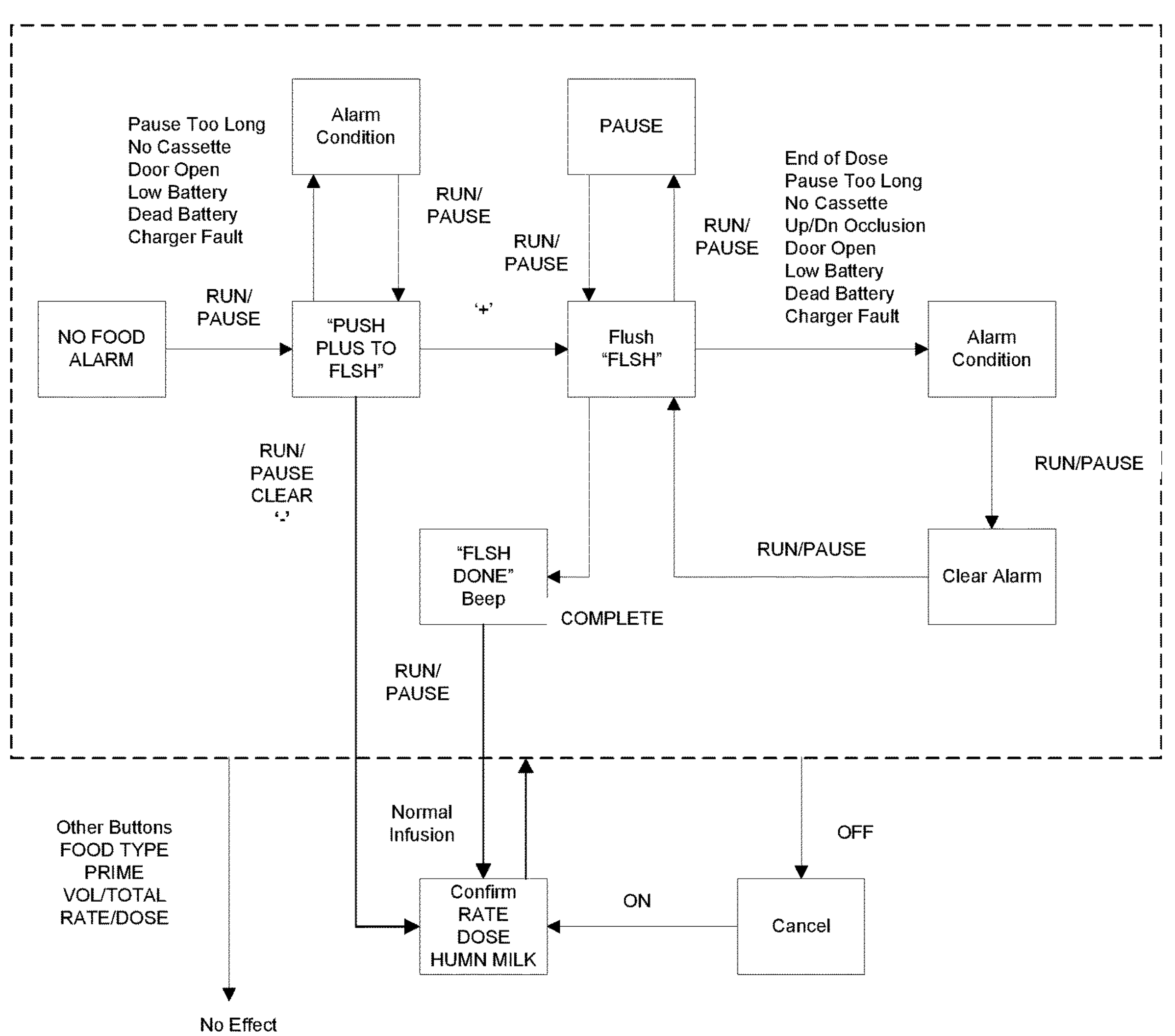
FIG. 5 is a schematic diagram illustrating functionality of a user interface of the pump when the pump is in the flush mode in accordance with an embodiment of the present disclosure.

FIGS. 3-5 generally illustrate process flow and logic associated with a flush mode of pump 10 according to an aspect of the present disclosure. As indicated in block 40, microprocessor 30 may be programmed to present a choice to the user upon determining that an end of therapy condition has been reached. The end of therapy condition may be determined if the signal from AIL sensor 26 indicates that an uninterrupted volume of air exceeding a predetermine threshold volume has passed through the interrogation zone of the AIL sensor. Microprocessor 30 may be programmed to issue an AIL alarm when this occurs. Alternatively, or additionally, determination of an end of therapy condition may be based on whether a liquid volume or liquid level in liquid source 19 has dropped below a threshold volume or level. The choice may be presented to the user by displaying a Confirm Flush message screen on display 34 prompting the user to confirm that flushing mode operation is desired by pressing a specific key or button, for example the "+" button.

In decision block 42, flow will branch depending upon which button of the user interface 32 is pressed by the user. For example, if the "+" button is pressed, pump 10 will enter the flush mode and a Flushing screen may be displayed by display 34 and an audible signal (e.g. a beep) may be issued by audible signal generator 35. However, if the user presses the "−" button, the CLEAR button, or the RUN/PAUSE button, the software logic treats the therapy as completed and flush mode is not entered.

When pump 10 is in the flush mode, the software causes microprocessor 30 to override the AIL alarm and command motor controller 36 to operate motor 20 to deliver a predetermined volume of liquid corresponding to a volume of liquid expected to remain in downstream tubing 8. The predetermined delivery volume may be calculated based on the programmed threshold volume of air required to trigger the AIL alarm, and the total volume of the lumen running through downstream tubing 8, which is known from the use of an administration set 18 authorized and designed for use with pump 10. For example, if pump 10 is applicant's INFINITY ORANGE® small volume enteral feeding pump used for infant feeding, the predetermined delivery volume may be set at 1.2 milliliters.

The predetermined delivery volume may be delivered in one continuous delivery until complete. However, it may be advantageous to deliver the predetermined delivery volume in increments, as indicated by block 44 in FIG. 3, wherein the pump motor is commanded to stop after an increment is delivered. Decision block 46 branches flow back to decision block 42 for further input from the user, unless all increments have been delivered, in which case the therapy is ended. In this way, the user has an opportunity to cancel delivery of further increments if the liquid has already reached the end of downstream tubing 8. Breast milk in particular is foamy at the transition from milk to air, making it difficult to determine how far milk has been pumped down the tubing. By commanding the motor to deliver residual liquid in increments, the user is intentionally involved in the flush mode delivery. In the example illustrated by FIG. 3, the total predetermined delivery volume may be delivered in four equal increments. Of course, microprocessor 30 may be programmed to use a different number of pumping increments, and the pumping increments may vary in volume.

The user may also pause delivery in the flush mode while motor 20 is operating by pressing the RUN/PAUSE button, and resume the delivery by again pressing the RUN/PAUSE button.

If an alarm (e.g. an occlusion alarm) is detected while the pump is delivering liquid in the flush mode, pumping may be paused and an alarm message may be displayed. In this case, the RUN/PAUSE button may be pressed to clear the alarm, and pressed again to resume flush mode pumping until the full residual amount is delivered.

The remaining liquid may be delivered at the programmed delivery rate. Pump may also have a separate programmed rate to deliver the downstream volume, or the remaining liquid may be delivered at the same rate as priming.

Once the additional pumping is finished, microprocessor 30 may be programmed to display a Flush Done screen on display 34 and issue another audible signal (e.g. another beep) by means of audible signal generator 35. If the Flush Done screen is showing and the user presses the RUN/PAUSE button, the programming instructions may treat the therapy as being ended. The residual delivery volume may count toward a programmed total dosage volume. If the total dosage volume is reached during the flush mode operation, the program instructions will stop the flush mode by causing a microprocessor to issue a motor stoppage command, and the software will consider the therapy ended.

As may be understood, the present disclosure may apply to an intravenous (IV) pump. As it is now, the liquid in the downstream tubing is discarded. The IV pump could use a similar algorithm to deliver the remaining liquid in the downstream tubing after an AIL condition is detected. If a specific dose is required of an IV pump, the pump may be programmed to deliver that dose minus the administration set priming volume, and then deliver the rest of the liquid according to the disclosed flush mode to achieve the correct dose. This would prevent the current need to discard the downstream volume of the drug.

In a further embodiment, microprocessor 30 may be programmed to enter the flush mode at the command of a user without having detected AIL.

Instead of delivering the remaining nutrition with whatever is currently in downstream tubing 8, a flush switchover mechanism may be used to switch to hydration and deliver the remaining nutrition by pumping water.

In a further embodiment, an AIL sensor 26 may be provided at the delivery end of downstream tubing 8 or at the opening of a gastrointestinal (GI) feeding tube connected to the patient to provide a signal to microprocessor 30, and microprocessor 30 may be programmed to automatically terminate the flush mode when a predetermined threshold volume of air is detected at the patient delivery end.

The present disclosure teaches methods and a pump apparatus configured by software programming to perform the methods. The disclosure teaches pump control algorithms which allow caregivers to use the last remaining liquid within downstream tubing. Example embodiments of the methods and pump apparatus of the present disclosure are described in detail herein, however those skilled in the art will realize that modifications may be made without straying from the scope of the disclosure.

What is claimed is:

1. A pumping system for delivering a liquid to a patient according to a predetermined therapy protocol, the pumping system comprising:

a source of the liquid;

an administration set for carrying the liquid from the source to the patient, the administration set including a tubing segment, upstream tubing communicating from the source to the tubing segment, and downstream tubing communicating from the tubing segment to the patient;

a pumping mechanism arranged to engage the tubing segment, the pumping mechanism including at least one pumping member, a motor operable to actuate the at least one pumping member to peristaltically deform the tubing segment to force the liquid through the tubing segment in a direction from the upstream tubing toward the downstream tubing, and a motor controller providing control commands to the motor;

a processor connected to the motor controller;

at least one sensor associated with the administration set and/or the source for generating an end-of-therapy signal indicating an end-of-therapy condition, wherein the end-of-therapy signal is transmitted to the processor;

at least one memory module including stored program instructions executable by the processor for operating the motor to control operation of the pumping mechanism; and a display connected to the processor;

wherein the stored program instructions include a flush mode routine executable by the processor to operate the pumping mechanism in a flush mode to deliver residual liquid present within the downstream tubing to the patient after the processor receives the end-of-therapy signal;

wherein execution of the flush mode routine is initiated in response to a user input action;

wherein the stored program instructions include an end-of-therapy routine executable by the processor to stop operation of the pumping mechanism and provide a prompt for the user input action on the display, wherein the end-of-therapy routine is executed in response to the end-of-therapy signal;

wherein execution of the flush mode routine delivers no more than a predetermined volume of liquid corresponding to a volume of liquid expected to remain in the downstream tubing after operation of the pumping mechanism is stopped in response to the end-of-therapy signal;

wherein execution of the flush mode routine delivers a first preprogrammed incremental portion of the predetermined volume of liquid and then automatically pauses operation of the pumping mechanism, wherein delivery of a further preprogrammed incremental portion of the predetermined volume of liquid is initiated in response to another user input action and termination of the flush mode routine is carried out in response to a user input cancellation action.

2. The pumping system according to claim 1, wherein the pumping mechanism, the processor, and the at least one memory module are part of an infusion pump including a user interface having a plurality of keys or buttons, wherein the user input action is pressing one of the keys or buttons.

3. The pumping system according to claim 1, wherein execution of the flush mode routine pauses operation of the pumping mechanism in response to a user input pause action.

4. The pumping system according to claim 1, wherein the at least one sensor includes an air-in-line sensor associated with the tubing segment.

5. The pumping system according to claim 1, wherein the at least one sensor includes a liquid level or liquid volume sensor associated with the source of the liquid.

6. The pumping system according to claim 1, further comprising an air-in-line sensor associated with a distal end of the downstream tubing and connected to the processor for automatically terminating execution of the flush mode routine when a predetermined threshold volume of air is detected by the air-in-line sensor.

7. The pumping system according to claim 1, wherein the preprogrammed incremental portion of the predetermined volume of liquid is a proper fraction of the predetermined volume of liquid having an integer numerator and an integer denominator.

8. The pumping system according to claim 7, wherein the proper fraction is ¼.

9. A method for delivering a liquid to a patient according to a predetermined therapy protocol, the method comprising:

automatically operating a pumping mechanism in accordance with the predetermined therapy protocol to deliver the liquid from a source to the patient by way of an administration set;

detecting an end-of-therapy condition and automatically stopping operation of the pumping mechanism when the end-of-therapy condition is detected;

prompting a user regarding execution of a flush mode routine for operating the pumping mechanism to deliver residual liquid to the patient, the residual liquid being present within downstream tubing of the administration set located downstream from the pumping mechanism after operation of the pumping mechanism is stopped when the end-of-therapy condition is detected; and initiating execution of the flush mode routine in response to a user input action;

wherein execution of the flush mode routine delivers no more than a predetermined volume of liquid corresponding to a volume of liquid expected to remain in the downstream tubing after operation of the pumping mechanism is stopped when the end-of-therapy condition is detected;

wherein execution of the flush mode routine delivers a first preprogrammed incremental portion of the predetermined volume of liquid and then automatically pauses operation of the pumping mechanism, wherein delivery of a further preprogrammed incremental portion of the predetermined volume of liquid is initiated in response to another user input action and termination of the flush mode routine is carried out in response to a user input cancellation action.

10. The method according to claim 9, wherein execution of the flush mode routine pauses operation of the pumping mechanism in response to a user input pause action.

11. The method according to claim 9, further comprising detecting when a predetermined threshold volume of air passes a distal portion of the downstream tubing near the patient and automatically terminating execution of the flush mode routine when the predetermined threshold volume of air is detected.

* * * * *